US012678292B2

(12) United States Patent
Mattei et al.

(10) Patent No.: US 12,678,292 B2
(45) Date of Patent: Jul. 14, 2026

(54) INTRA-VERTEBRAL BODY DEVICE FOR VERTEBRAL KYPHOPLASTY WITH DUAL EXPANSION (CRANIO-CAUDAL AND MEDIO-LATERAL) CAPABILITY

(71) Applicants: Tobias A. Mattei, Eureka, MO (US); Nicholas Musgrave, St. Louis, MO (US)

(72) Inventors: Tobias A. Mattei, Eureka, MO (US); Nicholas Musgrave, St. Louis, MO (US)

( * ) Notice: Subject to any disclaimer, the term of this patent is extended or adjusted under 35 U.S.C. 154(b) by 40 days.

(21) Appl. No.: 18/785,071

(22) Filed: Jul. 26, 2024

(65) Prior Publication Data

US 2025/0057663 A1 Feb. 20, 2025

Related U.S. Application Data

(60) Provisional application No. 63/519,741, filed on Aug. 15, 2023.

(51) Int. Cl.
| | |
|---|---|
| *A61F 2/44* | (2006.01) |
| *A61F 2/46* | (2006.01) |
| *A61F 2/30* | (2006.01) |

(52) U.S. Cl.
CPC .......... *A61F 2/4425* (2013.01); *A61F 2/4601* (2013.01); *A61F 2002/30471* (2013.01); *A61F 2002/30518* (2013.01); *A61F 2002/443* (2013.01); *A61F 2002/4631* (2013.01)

(58) Field of Classification Search
CPC ........ A61F 2/4425; A61F 2/4601; A61F 2/44; A61F 2/4455; A61F 2/447; A61F 2002/30471; A61F 2002/30518; A61F 2002/443; A61F 2002/4631
See application file for complete search history.

(56) References Cited

U.S. PATENT DOCUMENTS

| | | | | |
|---|---|---|---|---|
| 6,723,126 | B1 * | 4/2004 | Berry | A61F 2/4455 606/247 |
| 8,137,401 | B2 * | 3/2012 | Stad | A61F 2/442 623/17.11 |
| 10,470,895 | B2 * | 11/2019 | Suddaby | A61F 2/447 |
| 11,304,821 | B2 * | 4/2022 | Berry | A61F 2/447 |
| 2018/0078384 | A1 * | 3/2018 | Suddaby | A61F 2/4611 |
| 2023/0118386 | A1 * | 4/2023 | Suddaby | A61F 2/441 623/17.12 |
| 2025/0057571 | A1 * | 2/2025 | Mattei | A61F 2/4455 |

* cited by examiner

*Primary Examiner* — Ellen C Hammond
(74) *Attorney, Agent, or Firm* — Sandberg Phoenix & von Gontard, P.C.

(57) ABSTRACT

An intra-vertebral body mechanical device for cement augmentation of a fractured vertebral body which has a plurality of upper plates and a plurality of lower plates. An expansion mechanism is operably connected between the upper plates and the lower plates. The expansion mechanism is operable to cause the plurality of upper plates to move to side-by-side relative positions increasing their combined surface area and to cause the plurality of lower plates to move to side-by-side relative positions increasing their combined surface area.

20 Claims, 3 Drawing Sheets

1

INTRA-VERTEBRAL BODY DEVICE FOR VERTEBRAL KYPHOPLASTY WITH DUAL EXPANSION (CRANIO-CAUDAL AND MEDIO-LATERAL) CAPABILITY

CROSS-REFERENCE TO RELATED APPLICATIONS

This patent application claims priority from provisional patent application Ser. No. 63/519,741, which was filed on Aug. 15, 2023.

BACKGROUND

Cement augmentation is a common technique for treating spinal fractures, for example a vertebral compression fracture (VCF), and restoring proper spine functioning. A compression fracture of a spinal vertebra is typically caused by a physical injury to the vertebra of a patient with osteoporosis. Osteoporosis is a disease of the vertebra that leaves the vertebra weak and brittle and prone to fracture. Vertebroplasty and kyphoplasty are two cement augmentation surgical procedures used to treat VCF.

The vertebroplasty cement augmentation process is a minimally invasive surgical process that involves first positioning the patient face down on a surgical table and providing local anesthesia to the affected spinal area or the area of the fractured vertebral body.

Two small puncture incisions are made in the back over the fractured vertebra. A tubular cannula containing a pointed trocar is then inserted through each incision and into the fractured vertebral body. A real time x-ray or fluoroscope is used to guide placement of the cannulas and trocars.

The trocars are then removed from the cannulas and a bone cement is injected through each cannula. The bone cement is injected directly into the interior of the fractured vertebral body. The bone cement is allowed to harden and fuse the fractured vertebral bone fragments to create an internal cast in the interior of the fractured vertebral body and thereby stabilize the fractured vertebral body.

A kyphoplasty procedure is very similar to a vertebroplasty procedure. In a kyphoplasty procedure, after the trocars are removed from the cannulas and before the injection of cement, a specialized balloon called a balloon tamp is first inserted through each cannula. The balloons at the tips of the cannulas are positioned in the interior of the fractured vertebral body and inflated to restore the height of the vertebral body. As the balloons are inflated, they compact the soft inner bone and create a cavity space in the interior of the fractured vertebral body and return the vertebral body to a natural height. The balloon tamps are then deflated. After deflating the balloon tamps and removal of the balloon tamps through the cannulas, the space created in the interior of the vertebral body by the balloons is filled with the bone cement. After being injected, the bone cement quickly hardens, creating an internal cast that stabilizes the vertebral body.

At the end of each procedure the cannulas are removed, and the incisions are treated.

Initial cement augmentation procedures merely involved the injection of the bone cement into the fractured vertebral body. However, recently, new techniques targeting reduction of vertebral collapse and vertebral remodeling before injection of the cement have been developed. These new techniques include the use of a mechanical cavity creator device that replaces the balloons used in kyphoplasty. The Osseofix System and the Stryker SPINEJACK® are each examples of such a device.

In the use of mechanical cavity creator devices, the devices are adjusted to reduced size configurations and are inserted through the cannulas and into the fractured vertebral body. Expansion actuators are then inserted through the cannulas and connected to the devices. The actuators are then operated, causing the devices to expand along the cranio-caudal axis. The expansion of the devices expands the fractured vertebral body and restores the vertebral body to the natural height dimension of the vertebral body. Cement is then injected to stabilize the vertebral body.

The use of such mechanical devices has been shown to be superior to balloon kyphoplasty in the amount of force the mechanical devices can apply to the collapsed vertebral body to restore the vertebral body and the spine to their original conditions.

However, because current mechanical devices have reduced size configurations for their insertion through cannulas and into the interior of the vertebral body, and are restricted to applying force along the cranio-caudal axis of the vertebral body, the devices when expanded engage with only very small percentages of the interior surface areas of the vertebral body above and below the devices.

The limited size of the device reduces the surface areas at the top and bottom of the device that come into contact with the upper and lower interior surfaces of the fractured vertebral body above and below the device, respectively. The smaller surface areas of contact at the top and bottom of the device limit the ability of the device to achieve adequate correction to the natural height of the fractured vertebral body when the device is expanded.

No current device has, as its main or substantial feature, a medio-lateral expansion capability or expansion transverse to the spine which produces an increase in the surface area of contact of the device with the upper and lower interior surfaces of the fractured vertebral body, a feature which would increase the likelihood of achieving deformity correction and a successful restoration of the natural height of the fractured vertebral body.

SUMMARY

The intra-vertebral body device of this disclosure is designed for use in cement augmentation procedures and was developed to improve the ability of a mechanical device to apply forces used in restoring a collapsed vertebral body to its natural height dimension and improve the height restoration capability of the mechanical device. This is achieved by the ability of the device to expand engagement surfaces at the top and bottom of the device in the transverse or medio-lateral direction. The mechanical device of this disclosure includes a system which enables dual expansion, both along the cranio-caudal axis and in the medio-lateral direction as needed.

The intra-vertebral body device of this disclosure is designed for use in cement augmentation procedures for treating spinal fractures such as a vertebral compression fracture (VCF) and restoring proper spine functioning. The intra-vertebral body device is constructed and operated in substantially the same manner as known mechanical devices to expand inside a fractured vertebral body in the cranio-caudal direction. However, the device is improved in that the device comprises upper and lower mechanisms at the top and bottom of the device, respectively, having overlapping plates or angularly adjacent plates. The plates of the mechanisms at the top and bottom of the device are movable from their overlapped or angularly adjacent positions laterally outward relative to each other. The plates are movable by sliding movements of the plates or pivoting movement of the plates relative to each other to achieve medio-lateral expansion of the plates and the expansion of the combined surface areas of the plates at the top and bottom of the device. The lateral expansion of the plates achieves an increase in the surface areas at the top and bottom of the device opposing the interior surfaces at the top and bottom of the fractured vertebral body. The intra-vertebral body device is then operated in substantially the same manner as known mechanical devices to expand inside a fractured vertebral body in the cranio-caudal direction.

Various different types of mechanisms are employed on the top and bottom of the device to achieve the medio-lateral expansion of the plates of the device and the resultant increase in the surface areas at the top and bottom of the device.

The features, functions and advantages of the intra-vertebral body device that have been discussed above can be achieved independently in various embodiments or may be combined in yet other embodiments, further details of which can be seen with reference to the following description and drawings.

DETAILED DESCRIPTION

Figures 1, 2, 3:
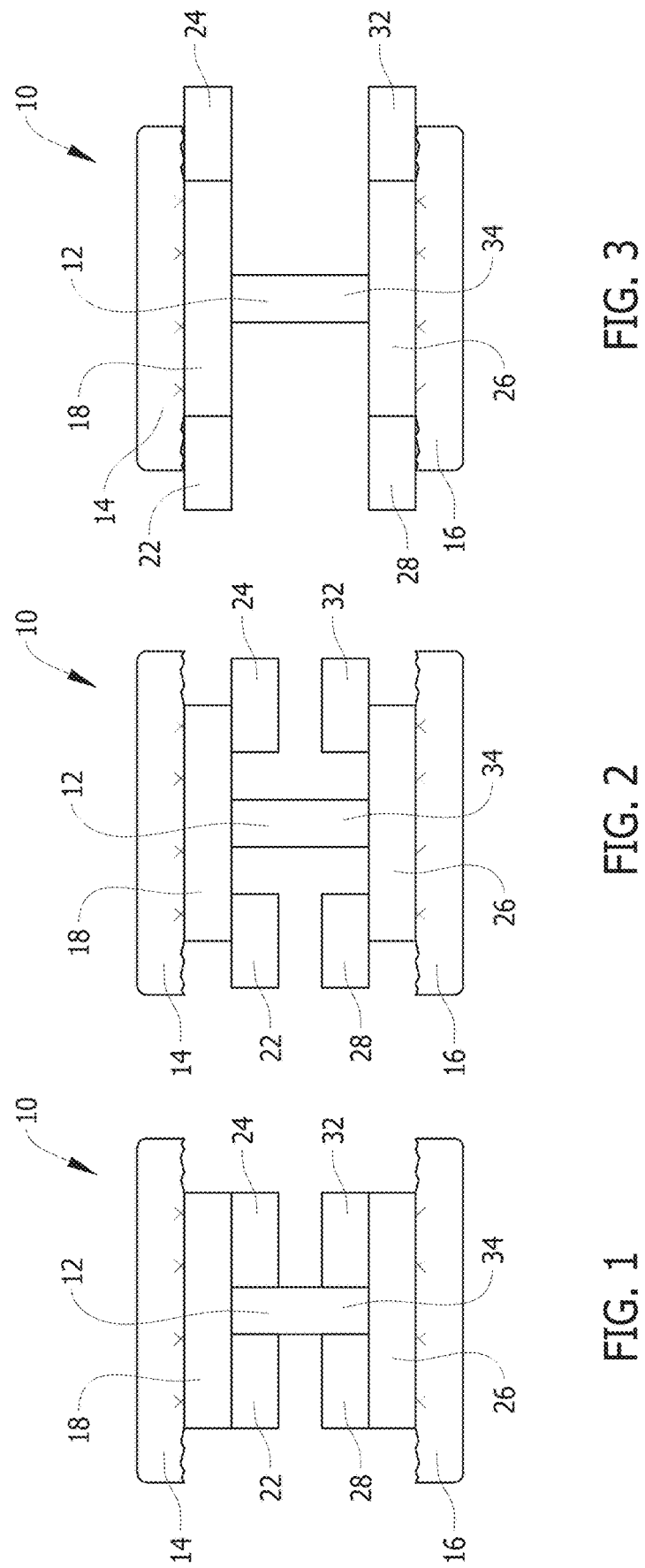
FIG. 1 is a schematic representation of an end elevation view of an embodiment of the intra-vertebral body device of this disclosure that has been surgically positioned in the interior of a fractured vertebral body. On the device of FIG. 1 the upper and lower plates are movable laterally from overlapped relative positions to laterally adjacent side-by-side relative positions.
FIG. 2 is a schematic representation of an end elevation view of an intermediate stage of the lateral movements of the plates of the device of FIG. 1.
FIG. 3 is a schematic representation of an end elevation view of the device of FIG. 1 in which the upper and lower plates have been moved to their laterally adjacent side-by-side positions.

A first embodiment of the intra-vertebral body device 10 of this disclosure is represented in FIG. 1, FIG. 2 and FIG. 3. The central component of the device is the base 12 which is expandable. The device 10 is represented as having been surgically positioned in the interior of a fractured vertebral body between an upper interior surface 14 and a lower interior surface 16 of the fractured vertebral body.

The base 12 has a longitudinal dimension between a top of the base and a bottom of the base that is adjustable. The base longitudinal dimension can be adjustably extended to be substantially the same natural height dimension of the fractured vertebral body. The base 12 also has a lateral dimension between a first side of the base and a second side of the base (the left and right sides of the base as viewed in FIG. 1) that is perpendicular to the longitudinal dimension. The base 12 also has a width dimension or a depth dimension between a front of the base and a rear of the base as viewed in FIG. 1. The longitudinal dimension of the base 12, with the base surgically positioned in the interior of the fractured vertebral body can be extended to cause the top of the base to engage and push against the upper interior surface 14 of the fractured vertebral body and cause the bottom of the base to engage and push against the lower interior surface 16 of the fractured vertebral body to restore the fractured vertebral body to its natural height dimension.

The intra-vertebral body device 10 also comprises of a plurality of upper plates 18, 22, 24 connected to the top of the base 12 and a plurality of lower plates 26, 28, 32 connected to the bottom of the base 10. The plates 18, 22, 24 and 26, 28, 32 are operatively connected to the top and bottom of the base 12, respectively, by an expansion mechanism 34 incorporated into the base 12 that enables lateral sliding movements of adjacent plates on the device.

The device 10 of FIGS. 1, 2 and 3 is intended to be inserted through a cannula in a reduced size configuration of the device in a manner similar to that employed in the insertion of other known mechanical devices such as those described earlier. Prior to insertion between the upper interior surface 14 of the fractured vertebral body and the lower interior surface 16 of the fractured vertebral body, the intra-vertebral body device 10 is adjusted to its compact configuration represented in FIG. 1. In the compact configuration the upper plates 18, 22, 24 and the lower plates 26, 28, 32 are adjusted to their overlapping and stacked relative positions. As represented in FIG. 1, in the compact configuration of the plurality of upper plates, the plurality of upper plates in the compact configuration comprise at least a first upper plate 18 positioned at the top of the base 12 or over the base 12 and second 22 and third 24 upper plates positioned in overlapping and stacked positions longitudinally below or underneath the first upper plate 14 and on laterally opposite sides of the base 12. As represented in FIG. 1, the second upper plate 22 and the third upper plate 24 are positioned entirely within the lateral dimension of the first upper plate 18 in the compact configuration of the plurality of upper plates. As represented in FIG. 1, in the compact configuration of the plurality of lower plates, the plurality of lower plates in the compact configuration comprise at least a first lower plate 26 positioned at the bottom of the base 12 or beneath the base 12 and second 28 and third 32 lower plates positioned at positions longitudinally above or longitudinally on top of the first lower plate 26 and on laterally opposite sides of the base 12. As represented in FIG. 1, the second lower plate 28 and the third lower plate 32 are positioned entirely within the lateral dimension of the first lower plate 26 in the compact configuration of the plurality of lower plates. On the base 12 represented in FIGS. 1, 2 and 3, each of the plates 18, 22, 24 and 26, 28, 32 has a rectangular configuration of substantially the same longitudinal, lateral and width dimensions. Adjacent plates are connected by tongue and groove connections that extend laterally and enable relative sliding movement of the adjacent plates laterally from the overlapping and stacked relative positions on the top and bottom of the base 12 represented in FIG. 1 to side-by-side relative positions represented in FIG. 3. Other equivalent connections that enable the lateral sliding movement of the plates 18, 22, 24 and 26, 28, 32 on the top and bottom of the base, 12 could be employed.

A rack and pinion expansion mechanism 34 incorporated into the base 12 could be operatively connected between adjacent plates 18, 22, 24 and 26, 28, 32 to cause the sliding and separating movements of the plates in response to rotation of a pinion gear. Alternatively, a compressed spring expansion mechanism 34 could be connected between adjacent plates 18, 22, 24 and 26, 28, 32 with a spring of the mechanism being compressed when the adjacent plates are in their overlapping and stacked relative positions represented in FIG. 1. By operation of an actuator of the compressed spring mechanism, the compressed spring can be released to move adjacent plates 18, 22, 24 and 26, 28, 32 laterally in sliding, separating relative movements represented in FIG. 2 to the side-by-side configuration of the adjacent plates represented in FIG. 3. Still further, other equivalent types of expansion mechanisms connected between the stacked adjacent plates 18, 22, 24 and 26, 28, 32 could be used to control movement of the plates laterally from the stacked relative positions represented in FIG. 1 to their side-by-side separated positions represented in FIG. 3.

FIG. 1 is a representation of the orientation of the intra-vertebral body device 10 once inserted into the interior of the fractured vertebral body between the upper interior surface 14 and the lower interior surface 16 of the fractured vertebral body. During the initial insertion of the device 10, the upper plates 18, 22, 24 and the lower plates 26, 28, 32 of the device 10 are in their overlapped or stacked relative positions on the top and bottom of the base 12, respectively. Once inserted into the interior of the fractured vertebral body, an instrument manipulated by the surgeon would be inserted into the interior of the fractured vertebral body and engaged with the expansion mechanism 34 incorporated in the base 12 to exert a torque on the expansion mechanism 34 which is operable to deploy the plates. For example, a clamp or grasper that engages a rotary actuator of the intra-vertebral body device 10 and manually rotates the actuator to cause the plates 18, 22, 24 and 26, 28, 32 to move laterally apart on the top and bottom of the base 12. Alternatively, a clamp or grasper could be used to manually operate an actuator of a spring device such as that described earlier. A simple surgical device in the form of a screwdriver could also be used to manually rotate or operate an actuator of the intra-vertebral body device 10 to initiate the sliding, separating movement of the plates 18, 22, 24 and 26, 28, 32 on the top and bottom of the base 12. Any equivalent type of actuator could be used to operate the sliding, separating movement of the plates 18, 22, 24 and 26, 28, 32 on the base 12.

To control the relative positions of the plates 18, 22, 24 and 26, 28, 32 during their lateral sliding, separating movements to position the plates in their side-by-side relative positions, the adjacent plates could have mechanical features such as tongue and groove connections or other equivalent connections that control the sliding and separating movement of the plates along linear paths.

As represented in FIG. 3, operation of the expansion mechanism 34 causes the upper plates 18, 22, 24 and the lower plates 26, 28, 32 to move laterally relative to each other and the base 12 to their expanded relative positions. In the expanded positions the upper plates 18, 22, 24 cover additional surface area of the upper, interior surface 14 of the fractured vertebral body at the top of the base 12, and the lower plates 26, 28, 32 cover additional surface area of the lower, interior surface 16 of the fractured vertebral body at the bottom of the base 12. The expansion mechanism 34 is configured to be operatively connected to the plurality of upper plates 18, 22, 24 and is configured to be operable to cause the plurality of upper plates to move from the compact configuration of the plurality of upper plates 18, 22, 24 represented in FIG. 1. The plurality of upper plates 18, 22, 24 move laterally relative to each other with the second 22 and third 24 upper plates moving laterally out from the overlapped and stacked positions below or underneath the first upper plate 18 represented in FIG. 2 to positions of the second upper plate 22 and the third upper plate 24 laterally aligned with and on laterally opposite sides of the first upper plate 18. The expansion mechanism 34 is configured to then move the second upper plate 22 and the third upper plate 24 longitudinally upward from below or beneath the first upper plate 18 to side-by-side positions of the second upper plate 22 and the third upper plate 24 laterally aligned with and on laterally opposite sides of the first upper plate 18 as represented in FIG. 3, thus achieving an increased combined surface area of the plurality of upper plates at the top of the base 12 with the combined surface area being configured to oppose additional surface area of the upper, interior surface 14 of the fractured vertebral body at the top of the base 12 when restoring a fractured vertebral body with the intra-vertebral body device 10. The expansion mechanism 34 is also operatively connected to the plurality of lower plates 26, 28, 32 and is configured to be operable to cause the plurality of lower plates to move from the compact configuration of the plurality of lower plates. 26, 28, 32 represented in FIG. 1. The plurality of lower plates 26, 28, 32 move laterally relative to each other with the second 28 and third 32 lower plates moving laterally out from the overlapped and stacked positions longitudinally above or on top of the first lower plate 26 represented in FIG. 2 to positions of the second lower plate 28 and the third lower plate 32 on the laterally opposite sides of the first lower plate 26. The expansion mechanism 34 is configured to then move the second lower plate 28 and the third lower plate 32 longitudinally downward from above or over the first lower plate 26 to side-by-side positions of the second lower plate 28 and the third lower plate 32 laterally aligned with and on laterally opposite sides of the first lower plate 26 as represented in FIG. 3, thus achieving an increased combined surface area of the plurality of lower plates at the bottom of the base 12 with the combined surface area being configured to oppose additional surface area of the lower, interior surface 16 of the fractured vertebral body at the bottom of the base 12 when restoring a fractured vertebral body with the intra-vertebral body device 10. The intra-vertebral body device 10 is then operated in substantially the same manner as known mechanical devices to expand inside the fractured vertebral body in the cranio-caudal direction or in the longitudinal direction.

As represented in FIG. 1, initially the upper plates 18, 22, 24 and lower plates 26, 28, 32 are positioned within the lateral and depth dimensions of the base 12 allowing for the smallest possible dimensions for intra-vertebral body device 10 insertion. The plates 18, 22, 24, 26, 28, 32 in their reduced size configuration are positioned within the 5-6 mm width of the device 10. This reduced size configuration is achieved by a shingling mechanism such that the individual plates 18, 22, 24, 26, 28, 32 are stacked on top of each other within the width dimensions of the device 10.

Figures 4, 5, 6:
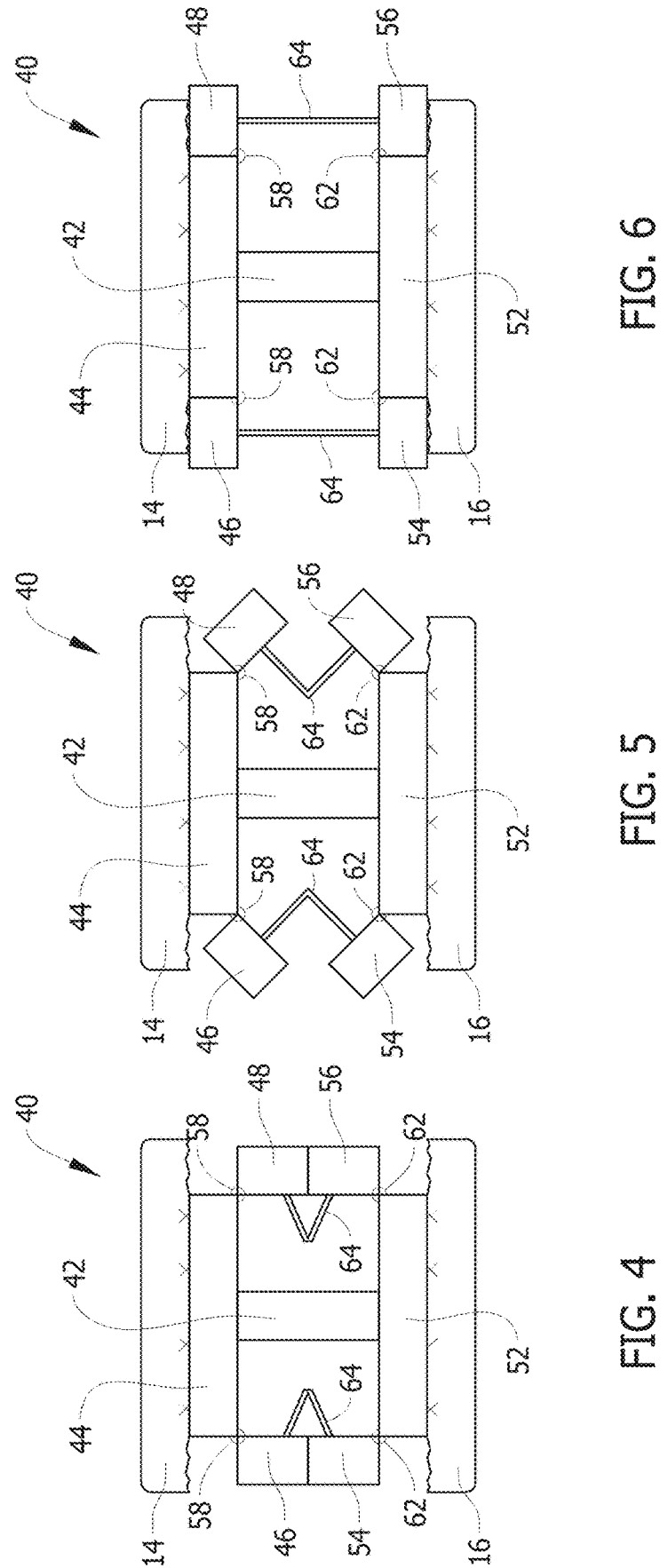
FIG. 4 is a schematic representation of an end elevation view of a further embodiment of the intra-vertebral body device of this disclosure that has been surgically positioned in the interior of a fractured vertebral body. On the device of FIG. 4 the upper and lower plates are movable in pivoting movements from general angled relative positions to laterally adjacent side-by-side relative positions.
FIG. 5 is a schematic representation of an intermediate stage of the lateral pivoting movement of the plates of the device of FIG. 4.
FIG. 6 is a schematic representation of an end elevation view of the intra-vertebral body device of FIG. 4 in which the upper and lower plates have been pivoted to their laterally adjacent side-by-side relative positions.

FIG. 4 is a representation of a further embodiment of the intra-vertebral body device 40 constructed in a similar manner to the intra-vertebral body device 10 of FIGS. 1, 2 and 3. In the intra-vertebral body device 40 represented in FIGS. 4, 5 and 6 the central component of the device 40 is the base 42. The base 42 has a longitudinal dimension between a top of the base and a bottom of the base. The base longitudinal dimension is substantially the same dimension as the natural height dimension of the fractured vertebral body. The base 42 also has a lateral dimension between a first side of the base and a second side of the base that is perpendicular to the longitudinal dimension. The base 42 also has a width dimension or a depth dimension between a front of a base and a rear of the base.

A plurality of upper plates 44, 46, 48 are connected to the top of the base 42 and a plurality of lower plates 52, 54, 56 are connected to the bottom of the base 42. The plates 44, 46, 48 and 52, 54, 56 are connected to the top and bottom of the base 42, respectively, by mechanisms that enable laterally outward pivoting movements of adjacent plates on the base 42.

Pivot connections 58, 62 enable achieving medio-lateral expansion of the upper plates 44, 46, 48 and the lower plates 52, 54, 56 of the intra-vertebral body device 40. The upper plates 44, 46, 48 are connected by pivot connections 58 to the base 42 and the lower plates 52, 54, 56 are connected by pivot connections 62 to the base 42. The intra-vertebral body device 40 of FIGS. 4, 5 and 6 employs an umbrella type actuation expansion mechanism 64 incorporated into the base 42 to control movements of the plates.

As the intra-vertebral body device 40 is inserted between the upper interior surface 14 and the lower interior surface 16 of the fractured vertebral body, the upper plates 44, 46, 48 and the lower plates 52, 54, 56 are connected through supporting expandable rods attached to a main cranio-caudal expanding strut of the expansion mechanism 64. The supporting expandable rods and the main strut are assembled together in a manner similar to that of an umbrella to form the expansion mechanism 64 of the intra-vertebral body device 40. As the strut of the device 40 is expanded in the cranio-caudal aspect or along the length of the spine, the rods 64 move the upper plates 44, 46, 48 to pivot laterally outward from the base 42 and relative to each other so that they are moved and pulled laterally outward to cover the medio-lateral surface of the upper interior surface 14 of the fractured vertebral body as represented in FIG. 5. Simultaneously, the rods move the lower plates 52, 54, 56 to pivot laterally outward relative to each other so that they are moved and pulled outward to cover the medio-lateral surface of the lower interior surface 16 of the fractured vertebral body as represented in FIG. 5. Alternatively, the expansion mechanism 64 could be operable by a rack and pinion actuator, a compressed spring actuator or any other equivalent type of actuator as those described earlier. The mechanism 64 does not necessarily need to rely on cranio-caudal expansion as the plates 44, 46, 48 and 52, 54, 56 could be initially contained by a locking mechanism which could be released through application of a torque by an insertion handle. In such a rendition of this embodiment, the plates 44, 46, 48 and 52, 54, 56 could be deployed laterally first and then locked in place before cranio-caudal expansion of the device 40. Such an embodiment, when combined with currently available cranio-caudal technology for plate expansion, would allow greater forces to be applied to the upper and lower interior surfaces of the fractured vertebral body during cranio-caudal expansion or expansion along the length of the spine.

This embodiment of the intra-vertebral body device 40 could be packaged with the upper plates 44, 46, 48 and the lower plates 52, 54, 56 folded along the outside of the device 40, with the lateral inferior plates folded outside of the superior plates or with the laterally superior plates folded outside the inferior plates.

Figure 7:
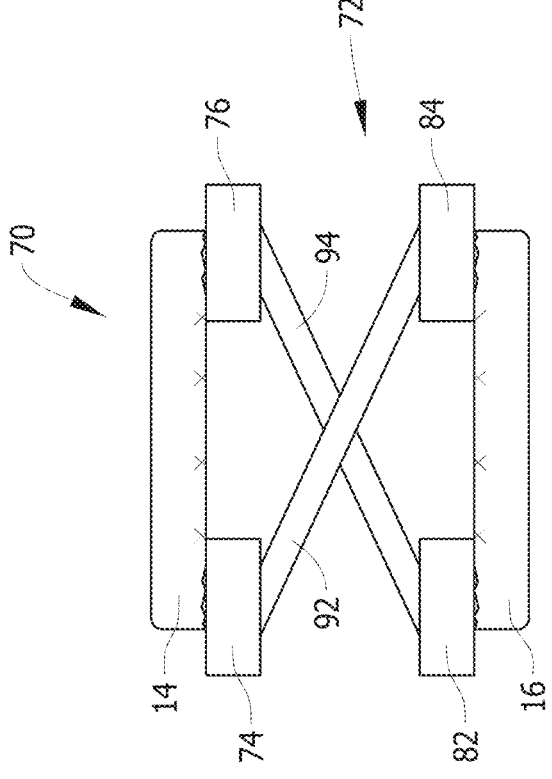
FIG. 7 is a schematic representation of an end elevation view of a still further embodiment of the intra-vertebral body device of this disclosure that has been surgically positioned in the interior of a fractured vertebral body. On the device of FIG. 7 the upper and lower plates are movable laterally from adjacent positions to laterally spaced side-by-side relative positions by extendable struts connected between the upper and lower plates.
Figure 8:
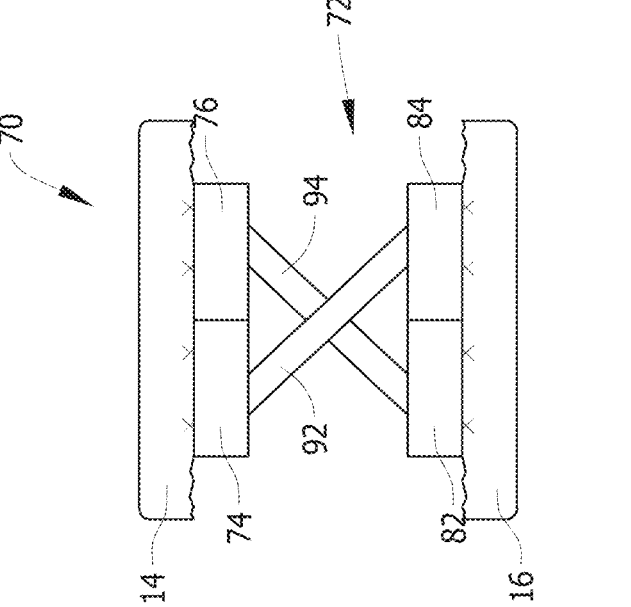
FIG. 8 is a schematic representation of an end elevation view of the intra-vertebral body device of FIG. 7 in which the upper and lower plates have been moved to their laterally spaced side-by-side relative positions.

FIG. 7 is a representation of a further embodiment of the intra-vertebral body device 70 through which medio-lateral expansion of the upper plates 74, 76 and lower plates 82, 84 can be achieved by involving a combination of the umbrella and overlapping plate mechanism, with an X shaped expandable strut structure expansion mechanism. As represented in FIG. 7, the intra-vertebral body device 70 is comprised of a base 72 with two upper plates 74, 76 connected to the top of the base 72 and two lower plates 82, 84 connected to the bottom of the base 72. The left side upper plate 74 is connected by an expandable strut 92 incorporated in the base 72 to the right side lower plate 84. The right side upper plate 76 is connected by an expandable strut 94 incorporated into the base 72 to the left side lower plate 82. Expansion of the struts 92, 94 can be achieved through the insertion and operation of a medical instrument such as those described earlier that can be manually manipulated to operate the expansion mechanism of the struts 92, 94. Operation of the expansion mechanism expands the lengths of the struts 92, 94 and results in the lateral movement of the upper plates 74, 76 away from each other and away from the base 72 and the lateral movement of the lower plates 82, 84 away from each other and away from the base 72. This results in the expansion of the intra-vertebral body device 70 in both the cranio-caudal direction and the medio-lateral direction until the upper surface of the device 70 defined by the upper plates 74, 76 and the lower surface of the device 70 defined by the lower plates 82, 84 are located in the same cranio-caudal plains of the upper interior surface 14 of the fractured vertebral body and the lower interior surface 16 of the fractured vertebral body as represented in FIG. 8.

Equivalent devices of those described deploy some form of plates medially and or laterally, while being initially located within the interior of a fractured vertebral body. The plates can be deployed in isolation to achieve only medio-lateral expansion or in combination with current technology for cranio-caudal expansion. In the case of combined expansion, the medio-lateral stage of expansion may occur before or after the cranio-caudal expansion. The devices may employ any form of ratcheting technique or torquing mechanism or any mode of expansion, performed either manually, through an insertion handle or through other mechanisms. The novelty of the devices is in the medio-lateral expansion of a standard intra-vertebral body device in order to increase the top and bottom surface areas covered by the intra-vertebral body device and, therefore, increase its capacity of restoring a natural height dimension to a fractured vertebral body.

As various modifications could be made in the construction of the intra-vertebral body devices and their methods of operation herein described and illustrated without departing from the scope of the inventions, it is intended that all matter contained in the foregoing description or shown in the accompanying drawings shall be interpreted as illustrative only rather than limiting. Thus, the breadth and scope of the present disclosure should not be limited by any of the above-described exemplary embodiments but should be defined only in accordance with the following claims appended hereto and their equivalents.

Procedure Description:

The patient undergoes general anesthesia and is placed in a prone position on a Jackson table with chest and hip pads. AP and lateral X-rays are brought in place in order to localize the level of the vertebrae in question. Then, the wound in the posterior or spinal region is prepped and draped. Stab incisions are performed approximately 3.5 cm off the midline on each side at the level in question. Jamshidi needles are inserted through the skin and progressed under the direct AP and lateral fluoroscopy until reaching the posterior portion of the pedicles of the vertebrae. Then, the Jamshidi needles are progressed until reaching the posterior portion of the vertebral body. AP and lateral fluoroscopy are obtained to demonstrate no violation of the pedicles. Then, the inner trocars of the Jamshidi needles are removed. K-wires are inserted. Jamshidi needles are removed. A drill is passed over the K-wire on both sides to create a cavity so that the intra-vertebral body implant could remodel the vertebral body. The drill is removed. A working cannula is inserted, and K-wire is removed. Then the new mechanical device is inserted through the cannula on both sides. Under live fluoroscopy the lateral wings or plates of the device are deployed through torque exerted through the insertion handle. After medio-lateral expansion the device is expanded in the cranio-caudal plane. AP and lateral fluoroscopy demonstrate adequate reduction of the superior endplate fracture with restoration of the vertebral body height. Then, methyl methacrylate is mixed and slowly injected through the working cannula under direct AP and lateral fluoroscopy. AP and lateral fluoroscopy demonstrate adequate distribution of the cement and restoration of the vertebral body height accomplishing a vertebral kyphoplasty. Then, the working cannulas are removed and the stab incisions are sutured with Monocryl 3-0. The wound is dressed with Dermabond.

The invention claimed is:

1. An intra-vertebral body device for restoring a fractured vertebral body comprising:

a base, the base having a longitudinal dimension between a top of the base and a bottom of the base, the top of the base and the bottom of the base being at longitudinally opposite ends of the base, the base longitudinal dimension between the top of the base and the bottom of the base is adjustable;

a plurality of upper plates operatively connected to the top of the base in a compact configuration of the plurality of upper plates, the plurality of upper plates in the compact configuration comprising at least a first upper plate positioned at the top of the base and second and third upper plates positioned in overlapping and stacked positions longitudinally beneath the first upper plate and on laterally opposite sides of the base;

a plurality of lower plates operatively connected to the bottom of the base in a compact configuration of the plurality of lower plates, the plurality of lower plates in the compact configuration comprising at least a first lower plate positioned at the bottom of the base and second and third lower plates positioned in overlapping and stacked positions longitudinally over the first lower plate and on laterally opposite sides of the base;

an expansion mechanism operatively connected to the plurality of upper plates and the plurality of lower plates;

the base, the plurality of upper plates, the plurality of lower plates and the expansion mechanism being configured for surgical positioning inside an interior of a fractured vertebral body between an upper interior surface of the fractured vertebral body and a lower interior surface of the fractured vertebral body, the expansion mechanism being configured to be operable to cause the plurality of upper plates to move from the compact configuration of the plurality of upper plates laterally relative to each other with the second and third upper plates moving laterally away from each other and out from the overlapped and stacked positions beneath the first upper plate, to positions of the second upper plate and the third upper plate on laterally opposite sides of the first upper plate and to move the second upper plate and the third upper plate longitudinally upward from beneath the first upper plate to side-by-side positions of the second upper plate and the third upper plate on laterally opposite sides of the first upper plate and achieve medio-lateral expansion of the plurality of upper plates and an expansion of the combined surface areas of the plurality of upper plates at the top of the base with the combined surface areas of the plurality of upper plates being configured to engage against and push against additional surface areas of the upper interior surface of the fractured vertebral body and the expansion mechanism being operable to cause the plurality of lower plates to move from the compact configuration of the plurality of lower plates laterally relative to each other with the second and third lower plates moving laterally away from each other and out from the overlapped and stacked positions over the first lower plate to positions of the second lower plate and the third lower plate on laterally opposite sides of the first lower plate and to move the second lower plate and the third lower plate longitudinally downward from over the first lower plate to side-by-side positions of the second lower plate and the third lower plate on laterally opposite sides of the first lower plate and achieve medio-lateral expansion of the plurality of lower plates and an expansion of the combined surface areas of the plurality of lower plates at the bottom of the base with the combined surface areas of the plurality of lower plates being configured to engage against and push against additional surface areas of the lower interior surface of the fractured vertebral body in restoring the fractured vertebral body with the intra-vertebral body device.

2. The device of claim 1, further comprising:

the expansion mechanism being configured to be operable to cause the plurality of upper plates to move from the overlapped, stacked relative positions of the first, second and third upper plates with the second and third upper plates positioned on laterally opposite sides of the base and the second and third upper plates positioned longitudinally beneath the first upper plate to side-by-side positions of the plurality of upper plates with the second and third upper plates positioned on laterally opposite sides of and laterally aligned with the first upper plate; and the expansion mechanism being configured to be operable to cause the plurality of lower plates to move from the overlapped, stacked relative positions of the first, second and third lower plates with the second and third lower plates positioned on laterally opposite sides of the base and the second and third lower plates positioned longitudinally over the first lower plate to the side-by-side positions of the plurality of lower plates with the second and third lower plates positioned on laterally opposite sides of and laterally aligned with the first lower plate.

3. The device of claim 2, further comprising:

the plurality of upper plates being operatively connected for relative linear sliding movement between adjacent plates of the plurality of upper plates; and the plurality of lower plates being operatively connected for relative linear sliding movement between adjacent plates of the plurality of lower plates.

4. The device of claim 3, further comprising:

the base, the plurality of upper plates, the plurality of lower plates and the expansion mechanism being adapted and configured for surgical insertion into an interior of a fractured vertebral body and then expanded longitudinally and medio-laterally.

5. The device of claim 3, further comprising:

the base, the plurality of upper plates, the plurality of lower plates and the expansion mechanism being adapted and configured for surgical insertion into an interior of a fractured vertebral body with the plurality of upper plates opposing an upper interior surface of the fractured vertebral body and the plurality of lower plates opposing a lower interior surface of the fractured vertebral body and then expanded longitudinally and medio-laterally.

6. The device of claim 1, further comprising:

the plurality of upper plates is separated from the plurality of lower plates by the expansion mechanism positioned longitudinally between the plurality of upper plates and the plurality of lower plates.

7. The device of claim 1, further comprising:

the expansion mechanism being configured to be operable to cause the plurality of upper plates to move relative to each other to side-by-side positions with the plurality of upper plates positioned on opposite sides of the top of the base; and the expansion mechanism being configured to be operable to cause the plurality of lower plates to move relative to each other to side-by-side positions with the plurality of lower plates positioned on opposite sides of the bottom of the base.

8. The device of claim 1, further comprising:

the expansion mechanism being configured to be operable to cause the plurality of upper plates to first move laterally from overlapped relative positions and then move longitudinally to adjacent side-by-side relative positions and to cause the plurality of lower plates to first move laterally from overlapped relative positions and then move longitudinally to adjacent side-by-side relative positions.

9. A device for intra-vertebral body restoration comprising:

a base, the base having a longitudinal dimension that is dimensioned for insertion between an upper interior surface of a fractured vertebral body and a lower interior surface of a fractured vertebral body, the base having a top of the base and a bottom of the base that are longitudinally spaced;

the base having a lateral dimension, the lateral dimension being mutually perpendicular with the longitudinal dimension;

a plurality of upper plates on the top of the base, the plurality of upper plates being connected to the top of a base in a compact configuration of the plurality of upper plates, the plurality of upper plates in the compact configuration comprising at least a first upper plate positioned at the top of the base and second and third upper plates position in overlapping and stacked positions longitudinally beneath the first upper plate and on laterally opposite sides of the base with the second upper plate positioned entirely below the first upper plate and the third upper plate positioned entirely below the first upper plate in the compact configuration of the plurality of upper plates, the plurality of upper plates on the top of the base being configured to be movable in a lateral direction on the top of the base and the plurality of upper plates on the top of the base being configured to be movable in a longitudinal direction on the top of the base; and a plurality of lower plates on the bottom of the base, the plurality of lower plates being connected to the bottom of the base in a compact configuration of the plurality of lower plates, the plurality of lower plates in the compact configuration comprising at least a first lower plate positioned at the bottom of the base and second and third lower plates positioned in overlapping and stacked positions longitudinally above the first lower plate and on laterally opposite sides of the base with the second lower plate positioned entirely above the first lower plate and the third lower plate positioned entirely above the first lower plate in the compact configuration of the plurality of lower plates, the plurality of lower plates on the bottom of the base being configured to be movable in the lateral direction on the bottom of the base and the plurality of lower plates on the bottom of the base being configured to be movable in the longitudinal direction on the bottom of the base.

10. The device of claim 9, further comprising:

the plurality of upper plates on the top of the base being movable in laterally sliding movements between adjacent upper plates on the top of the base.

11. The device of claim 10, further comprising:

the plurality of lower plates on the bottom of the base being movable in laterally sliding movements between adjacent lower plates on the bottom of the base.

12. The device of claim 11, further comprising:

tongue and groove connections between adjacent plates of the plurality of upper plates and adjacent plates of the plurality of lower plates.

13. The device of claim 9, further comprising:

the plurality of upper plates is separated from the plurality of lower plates by the expansion mechanism positioned vertically between the plurality of upper plates and the plurality of lower plates.

14. The device of claim 9, further comprising:

the expansion mechanism being configured to be operable to cause the plurality of upper plates to move relative to each other to side-by-side positions with the second upper plate and third upper plate of the plurality of upper plates positioned on opposite sides of the top of the base; and the expansion mechanism being configured to be operable to cause the plurality of lower plates to move relative to each other to side-by-side positions with the second lower plate and third lower plate of the plurality of lower plates positioned on opposite sides of the bottom of the base.

15. An intra-vertebral body device for restoring a fractured vertebral body comprising:

a base, the base having a longitudinal dimension that is configured for surgical positioning inside an interior of a fractured vertebral body between an upper interior surface and a lower interior surface of the fractured vertebral body, the base having a top of the base and a bottom of the base that are longitudinally spaced;

the base having a lateral dimension, the lateral dimension being mutually perpendicular with the longitudinal dimension;

a plurality of upper plates on the top of the base, the plurality of upper plates on the top of the base being movable laterally on the top of the base, the plurality of upper plates being connected to the top of the base in a compact configuration of the plurality of upper plates, the plurality of upper plates in the compact configuration comprising at least a first upper plate positioned at the top of the base and second and third upper plates positioned in overlapping and stacked positions longitudinally beneath the first upper plate with the second upper plate and the third upper plate positioned within a lateral dimension of the first upper plate and on laterally opposite sides of the base;

a plurality of lower plates on the bottom of the base, the plurality of lower plates on the bottom of the base being movable laterally on the bottom of the base, the plurality of lower plates being connected to the bottom of the base in a compact configuration of the plurality of lower plates, the plurality of lower plates in the compact configuration comprising at least a first lower plate positioned at the bottom of the base and second and third lower plates positioned in overlapping and stacked positions longitudinally over the first lower plate with the second lower plate and the third lower plate positioned within a lateral dimension of the first lower plate and on laterally opposite sides of the base; and an expansion mechanism inside the base operatively connected to the plurality of upper plates and the plurality of lower plates, the expansion mechanism being configured to be operable to cause the plurality of upper plates to move laterally relative to each other to side-by-side positions and achieve an increased combined surface area of the plurality of upper plates at the top of the base with the combined surface area being configured to oppose additional surface area of the upper interior surface at the top of the fractured vertebral body and to cause the plurality of lower plates to move laterally relative to each other to side-by-side positions and achieve an increased combined surface area of the plurality of lower plates at the bottom of the base with the combined surface area being configured to oppose additional surface area of the lower interior surface at the bottom of the fractured vertebral body in restoring the fractured vertebral body with the intra-vertebral body device.

16. The device of claim 15, further comprising:

the plurality of upper plates is separated from the plurality of lower plates by the expansion mechanism positioned longitudinally between the plurality of upper plates and the plurality of lower plates.

17. The device of claim 15, further comprising:

the expansion mechanism being operable to cause the plurality of upper plates to move from overlapped relative positions with the second and third upper plates positioned underneath the first upper plate to adjacent side-by-side relative positions and to cause the plurality of lower plates to move from overlapped relative positions with the second and third lower plates positioned on top of the first lower plate to adjacent side-by-side relative positions.

18. The device of claim 15, further comprising:

the base comprising the expansion mechanism.

19. The device of claim 15, further comprising:

the plurality of upper plates is operatively connected to the top of the base on opposite sides of the top of the base by the expansion mechanism incorporated into the base that enables relative movement of adjacent upper plates on the base; and the plurality of lower plates is operatively connected to the bottom of the base on opposite sides of the bottom of the base by the expansion mechanism incorporated into the base that enables relative movement of adjacent lower plates on the base.

20. The device of claim 15, further comprising:

the expansion mechanism being configured to be operable to cause the plurality of upper plates to first move laterally from overlapped relative positions and then move longitudinally to adjacent side-by-side relative positions and to cause the plurality of lower plates to first move laterally from overlapped relative positions and then move longitudinally to adjacent side-by-side relative positions.

* * * * *